United States Patent [19]

Barsom

[11] Patent Number: 4,580,578

[45] Date of Patent: Apr. 8, 1986

[54] DEVICE FOR THE TREATMENT OF FEMALE URINARY INCONTINENCE

[75] Inventor: Shafik Barsom, Hanover, Fed. Rep. of Germany

[73] Assignee: Richard Wolf GmbH, Knittlingen, Fed. Rep. of Germany

[21] Appl. No.: 606,998

[22] Filed: May 3, 1984

[30] Foreign Application Priority Data

May 6, 1983 [DE] Fed. Rep. of Germany ....... 3317118

[51] Int. Cl.$^4$ .............................................. A61N 1/04
[52] U.S. Cl. .................................................. 128/784
[58] Field of Search .................... 128/419 E, 784, 788, 128/793

[56] References Cited

U.S. PATENT DOCUMENTS

| 768,721 | 8/1904 | Bassell | 128/793 |
| 793,004 | 6/1905 | May | 128/793 |
| 3,866,613 | 2/1975 | Kenny et al. | 128/788 |

Primary Examiner—William E. Kamm
Attorney, Agent, or Firm—Hill, Van Santen, Steadman & Simpson

[57] ABSTRACT

The apparatus for treating female urinary incontinence operates on the principle of stimulating the sphincter muscles controlling the bladder with current impulses. The device comprises a supporting body (1) to which are attached two electrodes (3 and 4) having leads connected to an impulse generator (5). The supporting body (1) is fitted between the labia (7) in the region of the external urethral orifice (2) so that the electrodes have contact with the epidermal surface and are placed diametrically opposite each other on either side of the external urethral orifice (2). The electrodes (3 and 4) transmit the current impulses from the impulse generator (5) to the body tissues, whereby the muscular tissue of the sphincter (6) surrounding the urethra in this region is stimulated symmetrically and with precision and thus caused to contract. Involuntary excretion of urine is thus safely avoided. Due to the accurately targeted stimulation of the sphincter muscle, the supporting body (1) may be kept very small and adapted to the anatomy of the vulva. It is therefore hardly noticeable to the wearer and the intensity of current required to produce the necessary stimulus to the muscular tissue can be considerably reduced so that the risk of irritating the mucous membranes and body tissues is to a large extent eliminated. Lastly, the supporting body can be easily and quickly removed and therefore also easily cleaned (FIG. 1).

10 Claims, 6 Drawing Figures

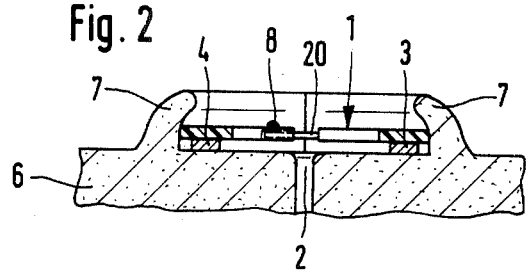
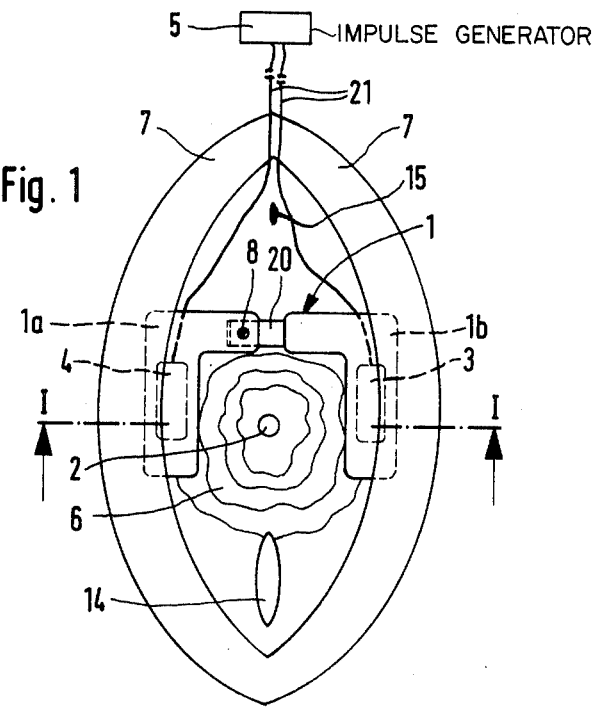
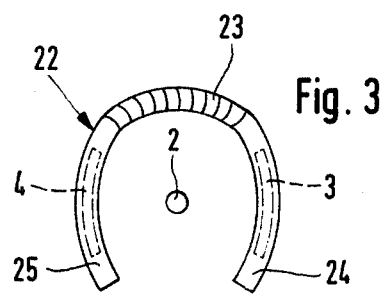

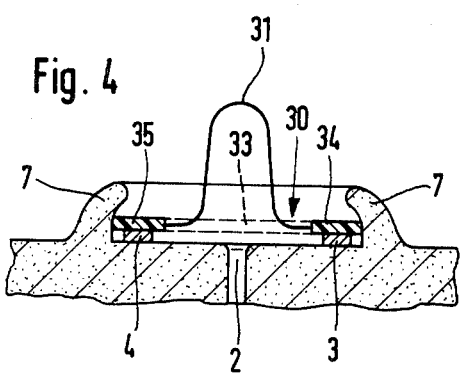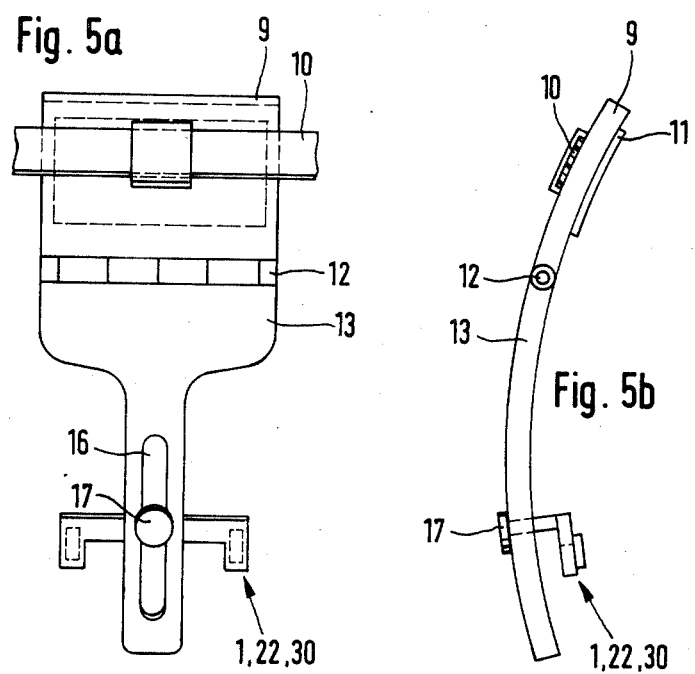

DEVICE FOR THE TREATMENT OF FEMALE URINARY INCONTINENCE

This invention relates to a device for the treatment of female urinary incontinence by stimulation of the sphincter muscles controlling the bladder, by means of current impulses. The device includes a supporting body to which are attached two electrodes having leads connected to an impulse generator.

Such devices are required for female subjects whenever the contractility of the circular sphincter muscles surrounding the urethra is impaired (e.g. as a result of pregnancy or due to ageing) so that involuntary loss of urine occurs. This impairment in function of the sphincter muscles may be counteracted by stimulating the muscular tissue of the sphincters to contraction by means of electric current impulses.

All previously known devices operating on this principle for the treatment of female urinary incontinence have a supporting body worn intravaginally and equipped with one or more than one pair of electrodes. The electrodes are subjected to a pulsating direct current which can be varied in the duration and intensity of the impulses and intervals between impulses so that the stimulation can be adapted individually to the damage of the sphincter muscle tissue of the patient. The form of the supporting body may vary in the known devices from a simple plug of hard synthetic resin (DE-PS 1 947 412) with an annular arrangement of electrodes surrounding the supporting body to plastics plugs more suitably adapted to the anatomy of the vagina (DE-OS 2 502 620) and even to a supporting body in the form of an elastic sleeve (DE-OS 2 717 956) in which the electrodes are arranged as points on the supporting body.

This intravaginal arrangement of the supporting body may at first sight appear to be very suitable but is in fact extremely disadvantageous. Firstly, the constant presence of a foreign body in the vagina may cause irritation of the mucous membrane and be experienced as highly unpleasant by the patient. Moreover, when the electrodes are arranged in the form of a ring round the supporting body, the muscular stimulation performed indirectly through the wall of the vagina has a diffuse action on the whole muscular tissue of the urethral and anal sphincters. If the electrodes are arranged as points, muscular stimulation is more accurately targeted on the sphincters controlling the bladder, but the electrodes in such an arrangement must be very accurately positioned in the vagina, and this makes the device more difficult to handle. In either case, relatively high current densities are required so that prolonged use may also cause irritation of the mucous membranes for this reason. Moreover, the muscles can only be stimulated from the side close to the vagina and therefore asymmetrically with respect to the sphincter muscles forming a ring round the urethra. There are also problems of hygiene which may be aggravated if scrupulous care is not taken to ensure that the surface of the supporting body is completely clean before its insertion in the vagina. Finally, there is the problem of increased risk of corrosion of the material of the supporting body due to its constant contact with the acid vaginal secretion.

It is an object of the present invention to provide a device for the treatment of female urinary incontinence obviating the disadvantages of the known devices and capable of being used accurately without insertion of a supporting body in the vagina.

To solve this problem accordng to the invention, the supporting body is designed to fit snugly against the vulva of the patient in a position between the labia in the region of the external urethral orifice, the two electrodes being arranged on the surface of the supporting body facing the vulva in a position diametrically opposite to each other on either side of the urethral orifice.

The arrangement of the supporting body between the labia as provided for the device according to this invention completely eliminates all the disadvantages resulting from an intravaginal arrangement of the supporting body and enables the treatment to be applied directly to the area of the lesion in the patient. The stimulation is directed very accurately to the sphincter muscle surrounding the urethra and acts symmetrically on this muscle.

The supporting body may be very small so that it is hardly noticed by the wearer. Since the device acts directly on the urethral sphincter, smaller currents are sufficient to stimulate the muscle. The risk of irritation to the mucous membranes and body tissues is therefore considerably reduced.

The supporting body also has the advantage of being easily removed and cleaned, and corrosive action on the material is substantially less than in the case of a supporting body arranged intravaginally since it is now not constantly in contact with body fluids.

Numerous embodiments and further developments of the invention are defined in the sub-claims and explained in more detail in descriptions of various embodiments given below with reference to the drawings, in which FIG. 1 is a top plan view of a preferred embodiment of the invention, FIG. 2 is a cross-sectional view taken on lines I—I of FIG. 1, in the direction I, FIG. 3 is a top plan view of an alternative embodiment of the invention, FIG. 4 is a cross-sectional of another embodiment of the invention and FIG. 5 shows means for fastening the device according to the invention with FIG. 5a being a plan view and FIG. 5b being a side view.

In the simplest form of the device according to the invention, the supporting body may be a flat disc of non-conductive and corrosion-resistant material, preferably a plastics material, on which the electrodes are arranged diametrically opposite to each other, taking the external urethral orifice as centre, on the side of the disc facing the patient's vulva. To facilitate unobstructed micturition during wear, the supporting body could be in the form of an annular disc, for example, but it is preferably designed to be adjustable to the width of the vulva of the individual wearer to ensure that it will be firmly seated between the labia. This may be achieved by various means.

In the embodiment according to FIGS. 1 and 2, the supporting body 1 is composed of two parts 1a and 1b to each of which is attached an electrode 3 or 4, respectively. The two parts of the supporting body are connected together at an adjustable distance apart. In the example illustrated, L-shaped attachments are provided on the two parts for this purpose, a bar 20 being fixed to the attachment on the part 1b to fit into a recess in the attachment on the other part, 1a, and a screw 8 is provided to fix the position of the bar 20. The supporting body 1 is therefore U-shaped in plan view.

By adjusting the distance between the parts, the supporting body 1 can be firmly fitted between the labia 7 in the region of the external urethral orifice 2 no matter what the individual width of the vulva. In this arrangement, as may be seen from FIG. 1, the supporting body is surrounded and partly covered by the labia. The supporting body is so arranged that the open end of the U faces the vaginal orifice 14 while the connecting web 20 is situated between the urethral orifice 2 and the clitoris 15.

The supporting body 1 and the parts 1a and 1b of which it is composed may have any geometrical form provided the device is securely seated between the labia. The substantially rectangular and flat form shown in FIGS. 1 and 2 has been chosen here mainly to simplify the drawing and facilitate the description of the function.

In practice, it is preferably to adapt the form of the supporting body to the anatomical structure to ensure that it will fit more comfortably and without pressure between the labia and avoid rubbing of the supporting body against the vulva. For this purpose, the supporting bodies 1a and 1b may, for example, be convexly curved on their external surfaces facing the labia, and the edges and corners may be rounded off.

In another embodiment of a supporting body 22 illustrated in FIG. 3, individual adjustment to the width of the vulva is achieved by replacing the rigid, adjustable bar 20 of FIGS. 1 and 2 by a connecting web 23 which is both flexible and elastic. The parts 24 and 25 of the body 22, corresponding to the parts 1a and 1b, are preferably again curved outwards on the sides facing the labia. The external diameter of the supporting body 22 (measured from one part 24 to the other 25) should be slightly greater than the distance between the labia 7. To insert the body 22 in the vulva, its external diameter is reduced by slightly pressing its parts 24 and 25 together, and when the pressure is subsequently released, the parts 24 and 25 will fit firmly against the labia without the need for any adjustment on the supporting body.

Firm contact of the supporting body against the labia may also be obtained by means of an expanding spring 31, as shown in FIG. 4. The supporting body 30 in this case is preferably similar to the supporting body 22 described above, comprising two parts 34 and 35 and an intermediate web 33, the expanding spring 31 acting between the parts 34 and 35 at the ends remote from the web 33. In this embodiment, the intermediate web need only be flexible and not elastic.

According to an alternative embodiment not shown here, the supporting body 30 may also be composed of two separate parts joined together only by one or more expanding springs without a connecting bar 20 or a connecting web 23 or 33.

When in use, the two electrodes 3 and 4 on the form of supporting body described in FIGS. 1 to 4 are arranged on the surface of the supporting part facing the vulva. This surface must be so designed that the electrodes in the vulva make as far as possible complete surface contact with the skin, and are preferably flat. A pulsating direct current is supplied to the two electrodes 3 and 4 from an impulse generator 5 by way of leads 21. The impulse generator contains a source of current in the form of an accumulator or a battery and delivers a current which is adjustable in its intensity of impulse, duration of impulse and interval time. The impuse preferably has an intensity of 3 mA and a duration and interval time of 1 to 30 seconds. The voltage of the source of current may be, for example, 9 Volt. The impulse generator 5 may be attached to the body of the patient, for example by means of a belt, or it may be carried in a pocket in a garment.

The slight skin moisture always present in the region of the vulva is sufficient to form a closed circuit of current passing between the electrodes 3 and 4 and through the body tissue including the muscular tissue of the sphincter 6 surrounding the urethra. The current impulses delivered from the electrodes stimulate the muscular tissue of the sphincter 6 causing it to contract and thus prevent any accidental excretion of urine.

The necessary contact of the electrodes 3 and 4 with the surface of the epidermis in the region of the urethral orifice 2 is normally provided by the firm fit of the supporting body against the labia 7 closely surrounding it and by the surface form of the supporting parts carrying the electrodes. If necessary, however, electrode contact may be further improved by means of a band or the like placed inside the briefs of the wearer to fit firmly over the supporting body and attached to the lower abdomen, for example by means of adhesive plaster. According to another embodiment, not illustrated here, small compression springs may be arranged between the electrodes 3 and 4 and the supporting body 1, 22 or 30, the force of the springs being adjusted, for example, by means of briefs fitting closely over the supporting body.

FIG. 5, comprising a top plan view (FIG. 5a) and a side view (FIG. 5b) shows a particular arrangement for fastening the supporting body 1, 22 or 30. This fastening device comprises a plate 9 connected to belt 10 and to a fastening arm 13 and may also be designed to carry the impulse generator 5. The supporting body is attached to the arm 13. The plate 9 is attached to the lower abdomen of the patient by means of the belt, for example above the pubic hairs, so that the supporting body on the arm 13 will be placed in the correct position for use. A rubber lining 11 on the back of the plate prevents the plate 9 from slipping out of position. To facilitate adjustment of the supporting body, the arm 13 may have a longitudinal slot 16 engaging with a slidable adjustment stop 17 which is attached to the supporting body and allows infinite adjustment of the position of this body.

The arm 13 is preferably not attached rigidly to the plate 9 but through a hinge 12. This enables the arm to be deflected upwards, away from the patient's body, for example for urinating or for cleaning the genital area or the supporting body, without the plate 9 having to be removed and subsequently readjusted.

When this fastening device is used, contact of the electrodes with the surface of the skin in the region of the vulva may again be assisted, as already described above, by an insert in the briefs, or the like, or by a small compression spring between the adjustment stop 17 and the supporting body. Furthermore, a spring may be provided in the hinge 12 to act on the fastening arm 13, urging it towards the vulva of the patient. This spring may be a dead centre spring so that when the fastening arm is swung away from the patient to a position beyond the dead centre point of the spring, the arm will be held in position there by the spring.

What is claimed is:

1. A device for the treatment of female urinary incontinence by stimulation of the sphincter muscle tissue controlling the bladder of a patient by means of current impulses, said device comprising: a supporting body having a flat shape with an upper surface, a lower flat surface and opposite lateral edges, two electrodes, said two electrodes being plate-like and being arranged on said lower flat surface in spaced relationship to each other and to be diametrically opposite each other; and an impulse generator connected to said electrodes so that with the lower flat surface of the supporting body fitting snugly against the vulva of the patient and the lateral edges against the labia in the region of the external urethral orifice, the electrodes engage the surface of the vulva on opposite sides of the external urethral orifice.

2. A device according to claim 1, wherein said supporting body is composed of two parts, one for each of the two electrodes, and means for connecting said two parts together with a variable spacing therebetween.

3. A device according to claim 2, wherein said means for connecting includes a bar to form a supporting body, and means for adjusting the length of said bar, said means for connecting and said two parts forming a supporting body having a U shape.

4. A device according to claim 2, wherein said means for connecting comprises an intermediate web, said web being both flexible and elastic, said web and two parts forming a supporting body having a U shape.

5. A device according to claim 2, wherein said means for connecting includes an expandable spring.

6. A device according to claim 1 which includes a plate and a fastening arm, said plate having means for fitting the plate on the body of said patient in the lower abdominal region thereof, said fastening arm being connected to the plate and being attached to the supporting body.

7. A device according to claim 6, wherein said fastening arm has a longitudinal slot, said device including stop means for mounting said supporting body by connecting to the upper surface of the supporting body, said stop means being adjustably positioned along said longitudinal slot.

8. A device according to claim 6 which includes hinge means for connecting the fastening arm to the said plate.

9. A device according to claim 8 which includes spring means in said hinge means to act on said fastening arm to urge said arm in one direction and towards the vulva of said patient.

10. A device according to claim 1, which includes pressure spring means being provided between said electrodes and said supporting body for urging the electrodes into contact with a surface of the vulva.

* * * * *